(12) United States Patent
Fu et al.

(10) Patent No.: US 12,223,225 B2
(45) Date of Patent: Feb. 11, 2025

(54) ATMOSPHERE ADJUSTING METHOD, ATMOSPHERE ADJUSTING DEVICE, AND AROMA DIFFUSER

(71) Applicant: SAVANT TECHNOLOGIES LLC, East Cleveland, OH (US)

(72) Inventors: Yao Fu, Shanghai (CN); Shan Liang, Shanghai (CN); Yin Suo, Shanghai (CN); Huisheng Zhou, Shanghai (CN)

(73) Assignee: SAVANT TECHNOLOGIES LLC, East Cleveland, OH (US)

( * ) Notice: Subject to any disclaimer, the term of this patent is extended or adjusted under 35 U.S.C. 154(b) by 636 days.

(21) Appl. No.: 17/517,540

(22) Filed: Nov. 2, 2021

(65) Prior Publication Data

US 2022/0137920 A1 May 5, 2022

(30) Foreign Application Priority Data

Nov. 2, 2020 (CN) .......................... 202011202697.2

(51) Int. Cl.
*A61L 9/015* (2006.01)
*G06F 3/16* (2006.01)

(52) U.S. Cl.
CPC .............. *G06F 3/165* (2013.01); *A61L 9/015* (2013.01); *A61L 2209/111* (2013.01)

(58) Field of Classification Search
CPC ......... A63G 31/16; G06F 3/165; G06F 40/58; A61L 9/015
USPC ...................................................... 472/60–61
See application file for complete search history.

(56) References Cited

U.S. PATENT DOCUMENTS

| | | |
|---|---|---|
| 2010/0168878 A1 | 7/2010 | Hoonhout et al. |
| 2014/0113715 A1 | 4/2014 | Joo et al. |
| 2018/0169288 A1 | 6/2018 | Kelsen |
| 2018/0341455 A1* | 11/2018 | Ivanov .................... G06F 40/58 |

FOREIGN PATENT DOCUMENTS

CN          209564436 U          11/2019

OTHER PUBLICATIONS

Office Action for Canadian Application No. 3,130,714 dated Oct. 3, 2023, 6 pages.

* cited by examiner

*Primary Examiner* — Kien T Nguyen

(57) ABSTRACT

The present application relates to an atmosphere adjusting method, an atmosphere adjusting device, and an aroma diffuser. The method comprising: receiving a recognition result of a smell for a specific position; obtaining a corresponding table that indicates a corresponding relationship between the recognition result of the smell and light and/or melody; determining the light and/or the melody to be output from the corresponding table, according to the recognition result of the smell; and instructing output of the corresponding light and/or melody. The technical solution of the application implements the adjustment of light and/or melody in response to the smell indoor, which makes the light and/melody change with the change of smell, thereby creating a harmonious and unified atmosphere in seeing, hearing and smelling for users.

34 Claims, 2 Drawing Sheets

ATMOSPHERE ADJUSTING METHOD, ATMOSPHERE ADJUSTING DEVICE, AND AROMA DIFFUSER

TECHNICAL FIELD

The present application relates to the field of atmosphere adjustment. Specifically, the present application relates to an atmosphere adjusting method, an atmosphere adjusting device, and an aroma diffuser for adjusting the atmosphere in a room.

BACKGROUND

Nowadays, people spend more and more time indoors. Aroma, high quality of light and pleasurable music can bring people a comfortable atmosphere. People usually use an aroma diffuser (or a fragrance lamp) to send out aroma in the room to eliminate the bad smell, make them feel happy and promote sleep. People play their favorite music through a stereo to improve their mood, and set indoor lights to heighten the atmosphere.

At present, some aroma diffusers have made it possible to emit suitable light while diffusing aroma, but the diffusion of the aroma and the light are controlled independently. For example, there are usually several preset lighting modes to choose, and people need to manually select a matching light color every time they change the essential oil. At present, some intelligent control systems have realized intelligent control of indoor lighting and music. This control works by presetting music matching a particular light and playing the music matching the particular light through a speaker when the particular light is emitted.

However, aroma and light and music are usually independently controlled and operated, and they cannot be controlled and adjusted in relation to each other. In particular, it is not possible to adjust the light and/or music in response to the smell in the room.

SUMMARY

The embodiments of the present application provide an atmosphere adjusting method, an atmosphere adjusting device and an aroma diffuser, which are used for adjusting the atmosphere in a room, so as to at least solve the problem in the prior art that light and/melody cannot be adjusted in response to a smell in a room.

According to an aspect of the embodiments of the present application, it is provided an atmosphere adjusting method which includes: receiving a recognition result of a smell for a specific position; obtaining a first corresponding table that indicates a corresponding relationship between the recognition result of the smell and light and/or melody; determining the light and/or the melody to be output from the first corresponding table, according to the recognition result of the smell; and instructing output of the corresponding light and/or melody.

In this way, it is possible to output the corresponding light and/or melody according to the smell of a specific position, so that when the smell changes, the light and/or the melody can change with the change of smell, thereby enable creating a harmonious and unified atmosphere in seeing, hearing and smelling for users.

In a schematic embodiment of the atmosphere adjusting method, the recognition result of the smell includes one or more of the following: smell molecules contained in the smell, a category to which the smell belongs, and a concentration of the smell.

In this way, it is possible to determine the light and/or the melody to be output according to the smell molecules contained in the smell, the category to which the smell belongs or the concentration of the smell, thereby realizing the adjustment of the light and/or the melody with the change of the smell.

In a schematic embodiment of the atmosphere adjusting method, determining the light and/or the melody to be output from the first corresponding table according to the recognition result of the smell includes: determining properties of the light and/or the melody, corresponding to the smell molecules contained in the smell, and/or the category to which the smell belongs, and/or the concentration of the smell from the first corresponding table; and determining the light and/or the melody to be output according to the determined properties of the light and/or the melody. The properties of the light include one or more of the following: color, lighting direction, degree of flicker and intensity, and the properties of the melody include one or more of the following: theme, genre, rhythm, pitch and intensity.

In this way, it is possible to determine the color, the lighting direction, the degree of flicker and the intensity of the light to be output according to at least one of the smell molecules contained in the smell, the category to which the smell belongs or the concentration of the smell, so that the light changes with the change of the smell; and/or it is possible to determine theme, the genre, the rhythm, the pitch and the intensity of the melody to be output according to at least one of the smell molecules contained in the smell, the category to which the smell belongs or the concentration of the smell, so that the melody changes with the change of the smell.

In a schematic embodiment of the atmosphere adjusting method, the first corresponding table includes a corresponding relationship between a combination of more than two kinds of smell molecules and the properties of the light and/or the melody.

In this way, with the first corresponding table, it is possible to determine the properties of the light and/or the melody to be output, according to the combination of more than two kinds of detected smell molecules existing in the environment, rather than a single kind of smell molecules.

In a schematic embodiment of the atmosphere adjusting method, the recognition result of the smell includes a plurality of kinds of smell molecules contained in the smell. Determining properties of the light and/or the melody corresponding to the smell molecules contained in the smell, and/or the category to which the smell belongs, and/or the concentration of the smell from the first corresponding table includes: determining the properties of the light and/or the melody corresponding to a combination of the plurality of kinds of smell molecules, from the first corresponding table.

In this way, when the received recognition result of the smell is a plurality of kinds of smell molecules contained in the smell, it is possible to determine the properties of the light and/or the melody directly corresponding to the combination of the plurality of kinds of smell molecules from the first corresponding table, thereby determining the light and/or the melody to be output.

In a schematic embodiment of the atmosphere adjusting method, the recognition result of the smell includes a plurality of kinds of smell molecules contained in the smell and concentration of the smell. The concentration of the smell includes the concentration of each kind of smell molecules in the plurality of kinds of smell molecules. Determining properties of the light and/or the melody corresponding to the smell molecules contained in the smell, and/or the category to which the smell belongs, and/or the concentration of the smell from the first corresponding table includes: determining the category to which the smell belongs from the first corresponding table, according to the plurality of kinds of smell molecules and the concentration of each kind of the smell molecules; and further determining the properties of the light and/or the melody corresponding to the category to which the smell belongs from the first corresponding table.

In this way, when the recognition result of the smell is the plurality of kinds of smell molecules contained in the smell and the concentration of the smell, it is possible to determine the category to which the smell belongs corresponding to the plurality of kinds of smell molecules and the concentration of each kind of the smell molecule, from the first corresponding table, and thus to determine the properties of the light and/or the melody to be output. That is, at this time, the first corresponding table includes a corresponding relationship between the plurality of kinds of smell molecules and the concentration thereof, and the category to which the smell belongs, and also includes a corresponding relationship between the category to which the smell belongs and the properties of the light and/or the melody.

In a schematic embodiment of the atmosphere adjusting method, determining properties of the light and/or the melody corresponding to the smell molecules contained in the smell, and/or the category to which the smell belongs, and/or the concentration of the smell from the first corresponding table further includes: according to a preset user preference, determining the properties of the light and/or the melody corresponding to the smell molecules contained in the smell, and/or the category to which the smell belongs, and/or the concentration of the smell from the first corresponding table.

In this way, it is possible to determine the properties of the light and/or the melody to be output by the user preference, in combination with the smell molecules, and/or the category to which the smell belongs, and/or the concentration of the smell included in the recognition result of the smell, so that the output light and/or melody conforms to the user preference while changing with the smell, thus facilitating creation of a user desired atmosphere.

In a schematic embodiment of the atmosphere adjusting method, determining the light and/or the melody to be output from the first corresponding table according to the recognition result of the smell includes: determining whether the concentration of the smell is higher than a preset first threshold or lower than a preset second threshold, the first threshold being greater than the second threshold; and when the concentration of the smell is higher than the first threshold, determining that the light and/or the melody to be output is a predetermined warning light and/or a warning tone; or when the concentration of the smell is lower than the second threshold, determining that the light and/or the melody to be output is a predetermined prompt light and/or a prompt tone.

In this way, one or both of the light and the melody may be used to inform the user of the smell at a specific position (for example, in a bathroom), thus facilitating creation of a desired atmosphere.

In a schematic embodiment of the atmosphere adjusting method, the method further includes: obtaining a second corresponding table that indicates a corresponding relationship between the recognition result of the smell and a smell to be diffused; determining a diffusion smell to be diffused from the second corresponding table according to the recognition result of the smell; and instructing diffusion of the diffusion smell.

In this way, it is possible to determine the diffusion smell to be diffused at a specific position according to the smell existing at the position, thereby facilitating creation of a desired atmosphere by the diffusion smell. The diffusion smell to be diffused may be the same as or different from the smell existing at the position.

In a schematic embodiment of the atmosphere adjusting method, instructing diffusion of the diffusion smell further includes: when the concentration of the smell received is lower than a preset third threshold, performing a control of increasing a diffusion rate of the diffusion smell until the concentration of the smell received reaching the third threshold; and when the concentration of the smell received is higher than a preset fourth threshold, performing a control of decreasing the diffusion rate of the diffusion smell until the concentration of the smell received being equal to or lower than the fourth threshold. The fourth threshold is greater than the third threshold.

In this way, it is possible to determine the diffusion rate of the diffusion smell to be diffused at the specific location according to the concentration of the smell existing at the position, so that the controlled concentration of the smell at the specific location is at the suitable level, thus facilitating creation of a desired indoor atmosphere.

In a schematic embodiment of the atmosphere adjusting method, the method further includes: obtaining position information of the specific position. Determining the light and/or the melody to be output from the first corresponding table according to the recognition result of the smell includes: determining the light and/or the melody to be output from the first corresponding table, according to the position information and the recognition result of the smell.

In this way, the light and/or the melody to be output is determined by the position information of the smell in combination with the recognition result of the smell, so that different lights and/or melodies can be set for different positions, that is, not only the light and/or the melody in the same room changes with the change of the smell, but also the light and/or the melody in different rooms varies depending on locations.

In a schematic embodiment of the atmosphere adjusting method, the method further includes: obtaining time information indicating the current time. The time information includes one or more of the following: a season of the year, a day of the week and a time of the day. Determining the light and/or the melody to be output from the first corresponding table according to the recognition result of the smell includes: determining the light and/or the melody to be output from the first corresponding table according to the time information and the recognition result of the smell.

In this way, the light and/or the melody to be output is determined by the current time information in combination with the recognition result of the smell, so that different lights and/or melodies can be set for different time, that is, the light and/or the melody at the specific location changes not only with the smell but also with time, thus creating a more harmonious atmosphere under consideration of impact of time on the atmosphere.

In a schematic embodiment of the atmosphere adjusting method, the method further includes: receiving a recognition result of one or more other smells for one or more other positions within a predetermined distance from the specified position. Determining the light and/or the melody to be output from the first corresponding table according to the recognition result of the smell comprises: determining the light and/or the melody to be output from the first corresponding table, according to the recognition result of the smell for the specific position and the recognition result of one or more other smells for one or more other positions.

In this way, the recognition result of the smells within a predetermined range (for example, in a living room) may be obtained accurately according to the recognition result of a plurality of smells in the predetermined range (for example, the recognition result of the smells received from a plurality of smell sensors at a plurality of different positions in the living room), so that the light and/or the melody corresponding to the smells within the range may be determined more accurately, so as to create a more harmonious and unified atmosphere.

According to another aspect of the embodiments of the present application, it is also provided an atmosphere adjusting device which includes: a controller; a smell sensor, configured to detect the smell at its position and output the recognition result of the smell; a lighting device and/or a music player, the lighting device is configured to output light according to the control of the controller, and the music player is configured to play a melody according to the control of the controller; and a memory, stored with a first corresponding table in advance, the first corresponding table indicates the corresponding relationship between the recognition result of the smell and the light and/or the melody. The controller is configured to receive the recognition result of the smell, obtain the first corresponding table from the memory, determine the light and/or the melody to be output from the first corresponding table according to the recognition result of the smell, and instruct the lighting device to output the corresponding light and/or instruct the music player to play the corresponding melody.

In this way, it makes the atmosphere adjusting device being able to output the corresponding light and/or melody according to the smell of the position where the smell sensor is, so that the light and/or the melody can change with the change of smell, thereby creating a harmonious and unified atmosphere in seeing, hearing and smelling for users.

In a schematic embodiment of the atmosphere adjusting device, the lighting device, the music player and the smell sensor are integrated in one device; or at least one of the lighting device, the music player or the smell sensor is set as a separate device.

In this way, the lighting device and/or the music player (as either or both exist) and the smell sensor may be set individually, or with two of them integrated, or with all of them integrated, so that makes it possible to arrange the positions of the lighting device and/or the music player and the smell sensor freely according to the environment and purpose of use, thus satisfying requirements of users for atmosphere adjustment better.

In a schematic embodiment of the atmosphere adjusting device, the number of each of lighting devices and/or music players and smell sensors is one or multiple. When the number of each of lighting devices and/or music players and smell sensors is multiple, each of the smell sensors is at a different position and corresponds to at least one lighting device and/or music player.

In this way, there may be one-to-one or one-to-multiple correspondence between the smell sensor and the lighting device and/or the music player, so that an appropriate number of lighting devices and/or music players and smell sensors may be set as needed to better create a harmonious and unified atmosphere in seeing, hearing and smelling for users. Moreover, when the multiple smell sensors are at different positions (for example, in different rooms in a home), the controller can also be used to simultaneously control the lights and/or melodies at the different positions to change with the smell, thus enabling the atmosphere adjusting device to adjust the atmospheres of multiple different environments.

In a schematic embodiment of the atmosphere adjusting device, the number of each of lighting devices and/or music players and smell sensors is one or multiple. When the number of each of lighting devices and/or music players and smell sensors is multiple, each of the lighting devices and/or music players is at the different position and corresponds to at least one smell sensor.

In this way, there may be one-to-one or one-to-multiple correspondence between the lighting device and/or the music player and the smell sensor, so that an appropriate number of lighting devices and/or music players and smell sensors may be set as needed to better create a harmonious and unified atmosphere in seeing, hearing and smelling for users. Moreover, when one lighting device and/or music player corresponds to multiple smell sensors, it is possible to determine the appropriate light and/or melody to be output for the environment where the multiple smell sensors are.

In a schematic embodiment of the atmosphere adjusting device, the recognition result of the smell includes one or more of the following: the smell molecules contained in the smell, the category to which the smell belongs, and the concentration of the smell.

In this way, it is possible to determine the light and/or the melody to be output according to the smell molecules contained in the smell, the category to which the smell belongs and the concentration of the smell, thereby realizing the adjustment of the light and/or the melody with the change of the smell.

In a schematic embodiment of the atmosphere adjusting device, determining, by the controller, the light and/or the melody to be output from the first corresponding table according to the recognition result of the smell includes: determining, by the controller, the properties of the light and/or the melody corresponding to the smell molecules contained in the smell, and/or the category to which the smell belongs, and/or the concentration of the smell from the first corresponding table; and determining the light and/or the melody to be output according to the determined properties of the light and/or the melody. The properties of the light include one or more of the following: color, lighting direction, degree of flicker and intensity, and the properties of the melody include one or more of the following: theme, genre, rhythm, pitch and intensity.

In this way, it is possible to determine the color, the lighting direction, the degree of flicker and the intensity of the light to be output according to at least one of the smell molecules contained in the smell, the category to which the smell belongs or the concentration of the smell, so that the light changes with the change of the smell; and/or it is possible to determine theme, the genre, the rhythm, the pitch and the intensity of the melody to be output according to at least one of the smell molecules contained in the smell, the category to which the smell belongs or the concentration of the smell, so that the melody changes with the change of the smell.

In a schematic embodiment of the atmosphere adjusting device, the first corresponding table includes the corresponding relationship between a combination of more than two kinds of smell molecules, and the properties of the light and/or the melody.

In this way, with the first corresponding table, it is possible to determine the properties of the light and/or the melody to be output according to the combination of more than two kinds of detected smell molecules existing in the environment, rather than a single kind of smell molecules.

In a schematic embodiment of the atmosphere adjusting device, the recognition result of the smell includes a plurality of kinds of smell molecules contained in the smell. Determining the properties of the light and/or the melody corresponding to the smell molecules contained in the smell, and/or the category to which the smell belongs, and/or the concentration of the smell from the first corresponding table includes: determining the properties of the light and/or the melody corresponding to the combination of the plurality of kinds of smell molecules from the first corresponding table.

In this way, when the received recognition result of the smell is the plurality of kinds of smell molecules contained in the smell, it is possible to determine the properties of the light and/or the melody directly corresponding to the combination of the plurality of kinds of smell molecules from the first corresponding table, thereby determining the light and/or the melody to be output.

In a schematic embodiment of the atmosphere adjusting device, the recognition result of the smell includes a plurality of kinds of smell molecules contained in the smell and the concentration of the smell. The concentration of the smell includes the concentration of each kind of smell molecules in the plurality of kinds of smell molecules. Determining the properties of the light and/or the melody corresponding to the smell molecules contained in the smell, and/or the category to which the smell belongs, and/or the concentration of the smell from the first corresponding table includes: determining the category to which the smell belongs from the first corresponding table according to the plurality of kinds of smell molecules and the concentration of each kind of the smell molecule; and further determining the properties of the light and/or the melody corresponding to the category to which the smell belongs from the first corresponding table.

In this way, when the recognition result of the smell is a plurality of kinds of smell molecules contained in the smell and the concentration of the smell, it is possible to determine the category to which the smell belongs corresponding to the plurality of kinds of smell molecules and the concentration of each kind of the smell molecule from the first corresponding table, thereby determining the properties of the light and/or the melody to be output. That is, at this time, the first corresponding table includes a corresponding relationship between the plurality of kinds of smell molecules and concentration thereof, and the category to which the smell belongs, and also includes a corresponding relationship between the category to which the smell belongs and the properties of the light and/or the melody.

In a schematic embodiment of the atmosphere adjusting device, the controller determines the properties of the light and/or the melody corresponding to the smell molecules contained in the smell, and/or the category to which the smell belongs, and/or the concentration of the smell from the first corresponding table further includes: according to the preset user preference, determining the properties of the light and/or the melody corresponding to the smell molecules contained in the smell, and/or the category to which the smell belongs, and/or the concentration of the smell from the first corresponding table.

In this way, it is possible to determine the properties of the light and/or the melody to be output by the user preference in combination with the smell molecules, and/or the category to which the smell belongs, and/or the concentration of the smell included in the recognition result of the smell, so that the output light and/or melody conforms to the user preference while changing with the smell, thus facilitating creation of a user desired atmosphere.

In a schematic embodiment of the atmosphere adjusting device, the controller determines the light and/or the melody to be output from the first corresponding table according to the recognition result of the smell includes: determining whether the concentration of the smell is higher than a preset first threshold or lower than a preset second threshold, the first threshold being greater than the second threshold; and when the concentration of the smell is higher than the first threshold, determining that the light and/or the melody to be output is a predetermined warning light and/or a warning tone; or when the concentration of the smell is lower than the second threshold, determining that the light and/or the melody to be output is a predetermined prompt light and/or a prompt tone.

In this way, one or both of the light and the melody may be used to inform the user of the smell at a specific position (for example, in a bathroom), thus facilitating creation of a desired atmosphere.

In a schematic embodiment of the atmosphere adjusting device, the device further includes: a smell diffusing device, which is configured to diffuse the smell according to the control of the controller. The memory stores in advance a second corresponding table that indicates a corresponding relationship between the recognition result of the smell and the smell to be diffused. The controller is further configured to obtain the second corresponding table, determine a diffusion smell to be diffused from the second corresponding table according to the recognition result of the smell, and instruct the smell diffusing device to diffuse the diffusion smell.

In this way, it is possible to determine the diffusion smell to be diffused at a specific position according to the smell existing at the position, thereby facilitating creation of a desired atmosphere by the diffusion smell. The diffusion smell may be the same as or different from the smell existing at the position.

In a schematic embodiment of the atmosphere adjusting device, instructing the smell diffusing device to diffuse the diffusion smell further includes: when the concentration of the smell received is lower than a preset third threshold, controlling the smell diffusing device to increase the diffusion rate of the diffusion smell until the concentration of the smell received reaching the third threshold; and when the concentration of the smell received is higher than a preset fourth threshold, controlling the smell diffusing device to decrease the diffusion rate of the diffusion smell until the concentration of the smell received being equal to or lower than the fourth threshold. The fourth threshold is greater than the third threshold.

In this way, it is possible to determine the diffusion rate of the diffusion smell to be diffused at the specific location according to the concentration of the smell existing at the position, so that the controlled concentration of the smell at the specific location is at the suitable level, thus facilitating creation of a desired indoor atmosphere.

In a schematic embodiment of the atmosphere adjusting device, the atmosphere adjusting device further includes: a position sensor, configured to sense the position of the smell sensor and output the position information of the smell sensor. The controller is further configured to obtain the position information of the smell sensor, and determine the light and/or the melody to be output from the first corresponding table according to the position information of the smell sensor and the recognition result of the smell.

In this way, the light and/or the melody to be output is determined by the position information of the smell in combination with the recognition result of the smell, so that different lights and/or melodies can be set for different positions, that is, not only the light and/or the melody in the same room changes with the change of the smell, but also the light and/or the melody in different rooms varies depending on locations.

In a schematic embodiment of the atmosphere adjusting device, the atmosphere adjusting device further includes: a clock module, configured to output the time information indicating the current time. The time information includes one or more of the following: a season of the year, a day of the week and a time of the day. The controller is further configured to obtain the time information, and determine the light and/or the melody to be output from the first corresponding table according to the time information and the recognition result of the smell.

In this way, the light and/or the melody to be output is determined by the current time information in combination with the recognition result of the smell, so that different lights and/or melodies can be set for different times, that is, the light and/or the melody at the specific location changes not only with the smell but also with time, thus creating a more harmonious atmosphere under consideration of impact of time on the atmosphere.

In a schematic embodiment of the atmosphere adjusting device, the atmosphere adjusting device further includes: one or more other smell sensors within a predetermined distance from the smell sensor, each configured to detect an other smell at its position and output the recognition result of the other smell. The controller determines the light and/or the melody to be output from the first corresponding table according to the recognition result of the smell includes: determining the light and/or the melody to be output from the first corresponding table according to the recognition result of the smell and the recognition results of one or more other smells.

In this way, the recognition result of the smells within a predetermined range (for example, in a living room) may be obtained accurately according to the recognition result of a plurality of smells in the predetermined range (for example, the recognition result of the smell received from a plurality of smell sensors at a plurality of different positions in the living room), so that the light and/or the melody corresponding to the smells within the range may be determined more accurately, so as to create a more harmonious and unified atmosphere.

In a schematic embodiment of the atmosphere adjusting device, the memory is a local memory or a network memory.

In this way, the first corresponding table and/or the second corresponding table may be stored in advance locally or on the network as needed, thus setting the atmosphere adjusting device more flexibly.

According to another aspect of the embodiments of the present application, it is also provided an aroma diffuser which includes: a controller, configured to perform the atmosphere adjusting method in the above; a smell sensor, configured to detect the smell at its position and output the recognition result of the smell; a lighting device, configured to output light according to the control of the controller; a music player, configured to play a melody according to the control of the controller; an essential oil diffusing device, includes an essential oil storage box and an essential oil diffuser, where the essential oil diffuser is configured to diffuse the essential oil in the essential oil storage box according to the control of the controller; and a memory, stored with a first corresponding table in advance, the first corresponding table indicates the corresponding relationship between the recognition result of the smell and the light and/or the melody.

In this way, it makes the aroma diffuser possible to output the corresponding light and/or melody according to the smell of environment, so that the light and/or the melody can change with the change of smell, thereby creating a harmonious and unified atmosphere in seeing, hearing and smelling for users.

In a schematic embodiment of the aroma diffuser, the smell of the essential oil includes top note, middle note and base note.

In this way, there is a fine change of top note, middle note and base note in the smell of the essential oil diffused into the surrounding environment. Through the fine change of the smell, a sense of hierarchy of the smell is created, which provides a richer user experience.

A schematic embodiment of the aroma diffuser, the controller respectively determines the light, and/or the melody, and/or the essential oil to be output according to the top note, the middle note and the base note of the essential oil.

In this way, by detecting the fine change of top note, middle note and base note in the smell of the essential oil through the smell sensor, the aroma diffuser enables the output light, and/or the melody, and/or the essential oil reflect the fine change in the smell of the essential oil, enables the output light and/or melody to have a sense of hierarchy, and enables the output essential oil to heighten the fine change in the smell of the existing essential oil, thereby not only creating a harmonious and unified atmosphere in seeing, hearing and smelling for users, but also bringing users a more immersive experience.

In a schematic embodiment of the aroma diffuser, the position of the smell sensor is any position on the outer surface of the aroma diffuser, so as to detect the smell outside of the aroma diffuser; or the position of the smell sensor is any position on a diffusion path of the essential oil in the aroma diffuser, so as to detect the smell inside the aroma diffuser.

In this way, the smell sensor can not only detect the smell in the external environment of the aroma diffuser, but also detect the smell in the internal environment of the aroma diffuser, so that the aroma diffuser can not only determine the light, and/or the melody, and/or the essential oil to be output according to the smell in the external environment, but also determine the light, and/or the melody, and/or the essential oil to be output according to the smell in the internal environment, which makes the output light, the played melody, and the diffused essential oil harmonious and unified.

In the embodiments of the present application, a technical solution is provided. In the technical solution, outputting the corresponding light and/or melody according to the smell at a specific position is implemented by receiving the recognition result of the smell for the specific position, obtaining the first corresponding table that indicates the corresponding relationship between the recognition result of the smell and the light and/or the melody, determining the light and/or the melody to be output from the first corresponding table according to the recognition result of the smell, and instructing output of the corresponding light and/or melody. Through the technical solution, the technical problem in the prior art that it is impossible to correspondingly adjust the light and/or melody for the smell in a room is solved, and the light and/or the melody may change with the smell, thereby creating a harmonious and unified atmosphere in seeing, hearing and smelling for users.

BRIEF DESCRIPTION OF THE DRAWINGS

The accompanying drawings described here are used for providing further understanding of the present application, and constitute a part of the present application. Schematic embodiments of the present application and description thereof are used for illustrating the present application and not intended to form an improper limit to the present application. In the accompanying drawings.

EXPLANATORY NOTES OF THE ACCOMPANYING DRAWINGS

Figure 1:
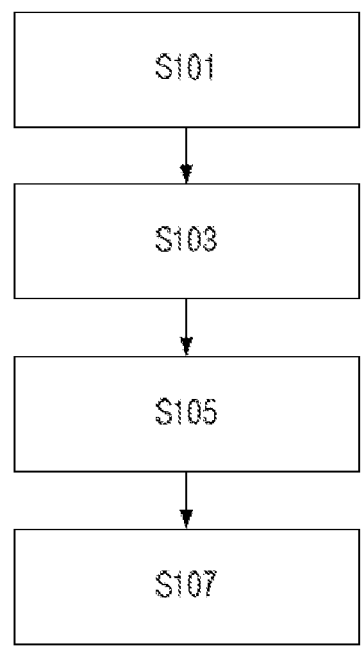
FIG. 1 is a flowchart of an atmosphere adjusting method according to an embodiment of the present application.

200: atmosphere adjusting device
300, 400: aroma diffuser
201, 301: controller
203, 303: lighting device
205, 305: music player
207, 307, 307': smell sensor
209, 311: memory
309: essential oil diffusing device
3091: essential oil storage box
3092: essential oil diffuser
S101: receiving a recognition result of a smell for a specific position;
S103: obtaining a corresponding table that indicates a first corresponding relationship between the recognition result of the smell and light and/or melody;
S105: according to the recognition result of the smell, determining the light and/or the melody to be output from the first corresponding table;
S107: instructing output of the corresponding light and/or melody.

DETAILED DESCRIPTION OF THE EMBODIMENTS

In order to make those skilled in the art understand the solutions of the present application better, the technical solutions in the embodiments of the present application are clearly and completely elaborated below in combination with the accompanying drawings. It is apparent that the described embodiments are only a part of the embodiments of the present application but not all. On the basis of the embodiment of the present application, all other embodiments obtained on the premise of no creative work of those skilled in the art should fall within the protection scope of the present application.

It is to be noted that the specification and claims of the application and terms "first", "second", etc. in the foregoing drawings are used for distinguishing similar objects rather than describing a specific sequence or a precedence order. It is to be understood that the objects may be exchanged under appropriate circumstances, so that the embodiments of the present application described here may be implemented in an order different from that described or shown here. In addition, terms "include" and "have" and any variations thereof are intended to cover non-exclusive inclusions. For example, it is not limited for processes, methods, systems, products or devices containing a series of steps or modules or units to clearly list those steps or modules or units, and other steps or modules or units which are not clearly listed or are inherent to these processes, methods, products or devices may be included instead.

According to an embodiment of the present application, an atmosphere adjusting method is provided. FIG. 1 is a flowchart of an atmosphere adjusting method according to an embodiment of the present application. As shown in FIG. 1, the atmosphere adjusting method may include the following steps.

At S101, receiving a recognition result of a smell for a specific position;

At S103, obtaining a corresponding table that indicates a first corresponding relationship between the recognition result of the smell and light and/or melody;

At S105, according to the recognition result of the smell, determining the light and/or the melody to be output from the first corresponding table; and At S107, instructing output of the corresponding light and/or melody.

In the present embodiment, the recognition result of the smell may be obtained from a smell sensor. The smell sensor detects and outputs the recognition result of the smell at its position, and the first corresponding table may be stored in a memory in advance.

In the present embodiment, the light is emitted by a lighting device (e.g., LED), and the melody is played by a music player (e.g., a speaker). The melody is a sequence of notes consisting of a series of notes with different or identical pitches that are associated with each other in a particular high and low relationship and rhythm relationship. The melody includes a warning tone, a prompt note and music.

In this way, it is possible to output the corresponding light and/or melody according to the recognition result of the smell, thereby the output light and/or melody may change with the change of the smell. By making the output light and/or melody correspond to the recognition result of the smell, the smell and the light and/or the melody are synchronized and mixed harmoniously, thereby creating a harmonious and unified atmosphere in seeing, hearing and smelling for users. Moreover, by making the output light and/or melody change with the change of the smell, a fine change of the smell can be magnified by using a dynamic change of the light and/or the melody, thereby bringing an immersive experience. For example, when the smell is the smell of perfume (or essential oil) used by a user, as the perfume usually presents different fragrances over time, such as lemon for the top note, lily for the middle note, and wood for the base note, through the atmosphere adjusting method in the present application, the output light and/or melody can change with the fine change of the smell, thereby bringing an immersive experience for users.

Further, in the present embodiment, the recognition result of the smell includes one or more of the following: smell molecules contained in the smell, a category to which the smell belongs, and a concentration of the smell. For example, all smell molecules exist in the air at the position of the smell sensor and the concentration of the smell molecules may be recognized by capturing gas molecules in the air through the smell sensor. The concentration of the smell includes the concentration of each kind of smell molecule. The category to which the smell belongs may be determined through a combination of all the smell molecules and the concentration of each kind of smell molecule. For example, the category may be ten basic categories of smell included in the full map of smells proposed by Dravnieks, that is, the odor of onion and garlic, sweet aroma, minty note, rotten smell, wood fragrance, aroma, fruit fragrance, chemical smell, smell of popcorn and lemon fragrance. The category may also be a further classified smell category. For example, aroma may further include mint fragrance, flower fragrance, soil fragrance and spicy fragrance, and the wood fragrance may further include vegetation fragrance and wooden fragrance.

In this way, it is possible to determine the light and/or the melody to be output according to one or more of the smell molecules contained in the smell, the category to which the smell belongs and the concentration of the smell, thereby realizing the adjustment of the light and/or the melody with the change of the smell.

Further, in the present embodiment, in S105, it may be determined, according to the recognition result of the smell, from the first corresponding table that only the light, or only the melody, or both the light and the melody are to be output.

Further, in the present embodiment, determining the light and/or the melody to be output from the first corresponding table according to the recognition result of the smell includes: determining properties of the light and/or the melody corresponding to the smell molecules contained in the smell, and/or the category to which the smell belongs, and/or the concentration of the smell from the first corresponding table; and determining the light and/or the melody to be output according to the determined properties of the light and/or the melody. The properties of the light include one or more of the following: color, lighting direction, degree of flicker and intensity, and the properties of the melody include one or more of the following: theme, genre, rhythm, pitch and intensity.

In this way, it is possible to determine the color, the lighting direction, the degree of flicker and the intensity of the light to be output according to at least one of the smell molecules contained in the smell, the category to which the smell belongs or the concentration of the smell, so that the light changes with the change of the smell; and/or it is possible to determine theme, the genre, the rhythm, the pitch and the intensity of the melody to be output according to at least one of the smell molecules contained in the smell, the category to which the smell belongs or the concentration of the smell, so that the melody changes with the change of the smell. Themes of the melody may include light music, love songs, folk songs, children's songs, festival songs, and so on. Genres of the melody may include classical, pop, rock, jazz, country, blues, rap, and so on.

Various corresponding relationships between the recognition result of the smell and the properties of the light and/or the melody may be stored in the first corresponding table. For example, different smell categories may correspond to light of different colors, such as, the mint fragrance corresponds to light blue light, the vegetation fragrance corresponds to green light, the flower fragrance corresponds to purple light, the soil fragrance corresponds to dark blue light, the citrus fragrance corresponds to light yellow light, the wooden fragrance corresponds to white light, and the spicy fragrance corresponds to red light.

For example, when the received recognition result of the smell indicates that the recognized smell belongs to the fruit fragrance with citrus note, according to the correspondence between non-flickering and high-intensity light yellow light and fruit fragrance with citrus note, which is stored in the first corresponding table, it may be determined that the non-flickering and high-intensity light yellow light is to be output, and output of the light through an LED lamp may be instructed. In this way, the output light and the present fruit fragrance with citrus note both bring a vivid and sunny atmosphere, a harmonious and unified atmosphere in seeing and smelling is created, and the atmosphere created by the smell is magnified by using the light.

For example, when the recognition result of the smell received indicates that the recognized smell belongs to the fruit fragrance with citrus note, based on the correspondence between the properties of the melody with theme of love song, the genre of pop, the rhythm of fast, the pitch of medium to high and the pitch of medium and the fruit fragrance with citrus note, which is stored in the first corresponding table, it may be determined that the melody in this format is to be output. The melody to be output may be stored locally in advance, or obtained from the network. In this way, the output melody and the present fruit fragrance with citrus note both bring a vivid and sunny atmosphere, a harmonious and unified atmosphere in hearing and smelling is created, and the atmosphere created by the smell is magnified by using the melody.

For example, when the recognition result of the smell received indicates that the recognized smell belongs to the gingerbread fragrance of Christmas, based on the correspondence between the subdivided theme of the melody, which is Christmas song, and the gingerbread fragrance stored in the first corresponding table, it may be determined that the melody with theme of Christmas song is to be output. Therefore, the output melody and the smell in together heighten the Christmas atmosphere.

Further, in the present embodiment, the first corresponding table includes the corresponding relationship between the combination of more than two kinds of smell molecules and the properties of the light and/or the melody.

In this way, with the first corresponding table, it is possible to determine the properties of the light and/or the melody to be output according to the combination of more than two kinds of detected smell molecules existing in the environment, rather than a single kind of smell molecules. As there is usually more than one kind of smell molecules in the actual environment, it makes the atmosphere adjusting method more consistent with actual usage.

Further, in the present embodiment, the recognition result of the smell includes the plurality of kinds of smell molecules contained in the smell. Determining the properties of the light and/or the melody corresponding to the smell molecules contained in the smell, and/or the category to which the smell belongs, and/or the concentration of the smell from the first corresponding table includes: determining, from the first corresponding table, the properties of the light and/or the melody corresponding to the combination of a plurality of kinds of smell molecules.

In this way, when the received recognition result of the smell only includes the plurality of kinds of smell molecules contained in the smell, it is possible to determine, from the first corresponding table, the properties of the light and/or the melody directly corresponding to the combination of a plurality smell molecules, thereby determining the light and/or the melody to be output. That is, the light and/or the melody to be output is determined only based on the plurality of kinds of smell molecules contained in the smell is implemented.

Further, in the present embodiment, the recognition result of the smell includes the plurality of kinds of smell molecules contained in the smell and the concentration of the smell. The concentration of the smell includes the concentration of each kind of smell molecules in the plurality of kinds of smell molecules. Determining the properties of the light and/or the melody corresponding to the smell molecules contained in the smell, and/or the category to which the smell belongs, and/or the concentration of the smell from the first corresponding table includes: determining the category to which the smell belongs from the first corresponding table, according to the plurality of kinds of smell molecules and the concentration of each kind of the smell molecule; and further determining, from the first corresponding table, the properties of the light and/or the melody corresponding to the category to which the smell belongs.

In this way, when the recognition result of the smell includes the plurality of kinds of smell molecules contained in the smell and the concentration of the smell, it is possible to determine the category to which the smell belongs corresponding to the plurality of kinds of smell molecules and the concentration of each kind of smell molecules from the first corresponding table, and thus determine the properties of the light and/or the melody to be output. That is, at this time, the first corresponding table includes a corresponding relationship between the plurality of kinds of smell molecules and concentrations thereof and the category to which the smell belongs, and also includes a corresponding relationship between the category to which the smell belongs and the properties of the light and/or the melody.

It is to be noted that the first corresponding table may also include the corresponding relationship between the plurality of kinds of smell molecules and the combination of their concentrations and the properties of the light and/or the melody. In this case, the corresponding properties of the light and/or the melody are determined directly from the first corresponding table, according to the plurality of kinds of smell molecules and the concentration of each kind of smell molecules.

Similarly, the recognition result of the smell may include only the category to which the smell belongs. Correspondingly, the first corresponding table includes the corresponding relationship between the category to which the smell belongs and the properties of the light and/or the melody, and thus the properties of the light and/or the melody to be output may be determined through the received category to which the smell belongs.

In a schematic embodiment of the atmosphere adjusting method, determining the properties of the light and/or the melody corresponding to the smell molecules contained in the smell, and/or the category to which the smell belongs, and/or the concentration of the smell from the first corresponding table further includes: according to a preset user preference, determining, from the first corresponding table, the properties of the light and/or the melody corresponding to the smell molecules contained in the smell, and/or the category to which the smell belongs, and/or the concentration of the smell.

In this way, it is possible to determine the properties of the light and/or the melody to be output by the user preference in combination with the smell molecules, and/or the category to which the smell belongs, and/or the concentration of the smell included in the recognition result of the smell, so that the output light and/or melody conforms to the user preference while changing with the smell, thus facilitating creation of a user desired atmosphere.

Further, in the present embodiment, determining the light and/or the melody to be output from the first corresponding table according to the recognition result of the smell includes: determining whether the concentration of the smell is higher than a preset first threshold or lower than a preset second threshold, the first threshold being greater than the second threshold; and when the concentration of the smell is higher than the first threshold, determining that the light and/or the melody to be output is a predetermined warning light and/or a warning tone; or when the concentration of the smell is lower than the second threshold, determining that the light and/or the melody to be output is a predetermined prompt light and/or a prompt tone.

In this way, one or both of the light and the melody may be used to inform the user of the smell at a specific location (for example, in a bathroom), thus facilitating creation of a desired atmosphere. For example, when the smell sensor located near a toilet detects an excessive concentration of smell from the toilet, the warning light and/or the warning tone may be used to warn the user of a bad smell in the bathroom, thus reminding the user to temporarily stop using the bathroom or take measures against the bad smell in the bathroom. For example, when the smell sensor in the living room with aromatherapy diffused detects a too low concentration of smell in the living room, the prompt light and/or the prompt tone may be used to remind the user to supplement an aromatherapy material or the water in which the aromatherapy material is dissolved.

Further, in the present embodiment, the method further includes: obtaining a second corresponding table that indicates a corresponding relationship between the recognition result of the smell and a smell to be diffused; determining the diffusion smell to be diffused from the second corresponding table, according to the recognition result of the smell; and instructing diffusion of the diffusion smell.

In this way, it is possible to determine the diffusion smell to be diffused at a specific location according to the smell existing at the location, thereby facilitating creation of a desired atmosphere by the diffusion smell. The diffusion smell may be the same with or different from the smell existing at the location. When the recognition result of the smell received indicates that the smell present at the location is a pleasant or desirable fragrance, it may be instructed that diffusing a smell identical to or similar to the smell. When the recognition result of the smell received indicates that the smell present at the location is an unpleasant odor, it may be instructed that diffusing a different smell. For example, when the recognition result of the smell received indicates that the smell is the gingerbread fragrance of Christmas, it may be determined that the diffusion smell is the gingerbread fragrance as well, or is other fragrances of other food that can represent Christmas, so as to further heighten the festive atmosphere. For example, when the recognition result of the smell received indicates that the smell is the rotten smell, it may be determined that the diffusion smell is the lemon fragrance, so as to cover up the rotten smell, and thus creating a user desired atmosphere.

Further, in the present embodiment, instructing diffusion of the diffusion smell further includes: when the concentration of the smell received is lower than a preset third threshold, performing a control of increasing a diffusion rate of the diffusion smell until the concentration of the smell received reaching the third threshold; and when the concentration of the smell received is higher than a preset fourth threshold, performing a control of decreasing the diffusion rate of the diffusion smell until the concentration of the smell received being equal to or lower than the fourth threshold. The fourth threshold is greater than the third threshold.

In this way, it is possible to determine the diffusion rate of the diffusion smell to be diffused at the specific location according to the concentration of the smell existing at the location, so that the controlled concentration of the smell at the specific location (for example, the living room) is at the suitable level, thus facilitating creation of a desired atmosphere.

Further, in the present embodiment, the method further includes: obtaining position information of the specific position. Determining the light and/or the melody to be output from the first corresponding table according to the recognition result of the smell includes: determining the light and/or the melody to be output from the first corresponding table according to the position information and the recognition result of the smell. At this time, the first corresponding table may include a corresponding relationship between the whole of the position information and the recognition result of the smell, and the light and/or the melody.

In this way, the light and/or the melody to be output is determined by the position information of the smell in combination with the recognition result of the smell, so that different lights and/or melodies can be set for different positions, that is, not only the light and/or the melody in the same room changes with the change of the smell, but also the light and/or the melody in different rooms varies depending on locations.

For example, when the obtained position information is bedroom and the recognition result of the smell received indicates that the recognized smell belongs to the fruit fragrance with citrus note, it may be determined from the first corresponding table that the light to be output is the light yellow light with no flicker and moderate intensity that illuminates the head of the bed. When the obtained position information is living room, and the recognition result of the smell received indicates that the recognized smell belongs to the fruit fragrance with citrus note, it may be determined from the first corresponding table that the light to be output is the light yellow light with no flicker and high intensity that illuminates all around.

In this way, the output light and the present fruit fragrance with citrus note not only bring a sunny atmosphere, but also present a quiet atmosphere in the bedroom and present a vivid atmosphere in the living room. That is, in the case of the same smell, different rooms present the output of different lights and/or melodies to create different desired atmospheres for different rooms. When the users walk into the different rooms, they can feel the desired atmosphere for different rooms, thus bringing more comfortable experience to the users.

Further, in the present embodiment, the method further includes: obtaining time information indicating the current time. The time information includes one or more of the following: a season of the year, a day of the week and a time of the day. Determining the light and/or the melody to be output from the first corresponding table according to the recognition result of the smell includes: determining the light and/or the melody to be output from the first corresponding table, according to the time information and the recognition result of the smell.

In this way, the light and/or the melody to be output is determined by the current time information in combination with the recognition result of the smell, so that different lights and/or melodies can be set for different times, thereby creating a more harmonious atmosphere taking into account not only the influence of smell on the atmosphere, but also the influence of time on the atmosphere.

At this time, the first corresponding table may indicate a corresponding relationship between the whole of the time information and the recognition result of the smell, and the light and/or the melody. The time information may be obtained from a local clock or a network clock.

Further, in this case, determining the light and/or the melody to be output from the first corresponding table according to the recognition result of the smell may further include: determining the light and/or the melody to be output from the first corresponding table, according to the position information, the time information and the recognition result of the smell. At this time, the first corresponding table may indicate a corresponding relationship between the whole of the position information, the time information and the recognition result of the smell, and the light and/or the melody.

For example, when the obtained position information is bedroom, the time is 8 p.m., and the recognition result of the smell received indicates that the recognized smell belongs to the fruit fragrance with citrus note, it may be determined from the first corresponding table that the light to be output is the light yellow light with no flicker and moderate intensity that illuminates all around.

In this way, not only the influence of smell and location on the atmosphere, but also the influence of time on the atmosphere is taken into account, thus creating a more harmonious atmosphere after the corresponding light and/or melody is output.

Moreover, as the time information is not limited to a time of the day, but also a season of the year, a day of the week, etc., the influence of time on the atmosphere may be refined to help achieve the harmonious atmosphere as the users desired.

Moreover, the diffusion smell to be diffused may also be determined from the second corresponding table, according to the position information and the recognition result of the smell, or according to the position information, the time information and the recognition result of the smell. At this time, the second corresponding table may indicate the corresponding relationship between the whole of the position information and the recognition result of the smell, and the smell to be diffused, and/or indicate the corresponding relationship between the whole of the location information, the time information and the recognition result of the smell, and the smell to be diffused.

In this way, the corresponding light, and/or melody, and/or smell may be output under the consideration of the influence of smell, location and time on the atmosphere, thus creating a more harmonious atmosphere.

In a schematic embodiment of the atmosphere adjusting method, the method further includes: receiving a recognition result of one or more other smells for one or more other positions within a predetermined distance from the specified position. Determining the light and/or the melody to be output from the first corresponding table according to the recognition result of the smell comprises: determining the light and/or the melody to be output from the first corresponding table, according to the recognition result of the smell for the specific position and the recognition result of one or more other smells for one or more other positions.

In this way, the recognition result of multiple smells within in a predetermined range may be used to accurately obtain the recognition result of the smell within the predetermined range (the smell and one or more other smells are within the predetermined range). For example, multiple smell sensors may be set at different positions in the living room, and the recognition result of the smell in the living room may be accurately determined by multiple recognition results of the smell received from the multiple smell sensors instead of the single recognition result of the smell received from a single smell sensor. Thus, the light and/or the melody corresponding to the smell within the predetermined range may be determined more accurately, so as to create a more harmonious and unified atmosphere.

Figure 2:
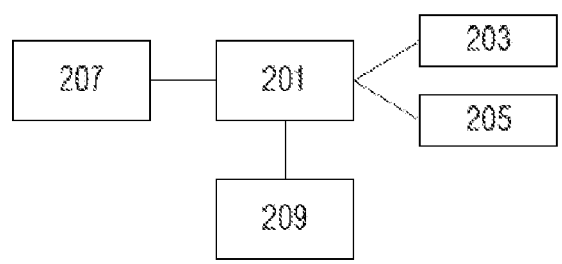
FIG. 2 is a block diagram of an atmosphere adjusting device according to an embodiment of the present application.

According to an embodiment of the present application, an atmosphere adjusting device is also provided. FIG. 2 is a block diagram of an atmosphere adjusting device according to an embodiment of the present application. As shown in FIG. 2, the atmosphere adjusting device 200 includes: a controller 201, a smell sensor 207, a lighting device 203 and/or a music player 205, and a memory 209. The smell sensor 207 is configured to detect the smell at its position and output the recognition result of the smell. The lighting device 203 is configured to output light according to the control of the controller 201, and the music player 205 is configured to play a melody according to the control of the controller. The memory 209 is configured to store the first corresponding table in advance. The first corresponding table indicates the corresponding relationship between the recognition result of the smell and the light and/or the melody. The controller 201 is configured to receive the recognition result of the smell, obtain the first corresponding table from the memory 209, determine the light and/or the melody to be output from the first corresponding table according to the recognition result of the smell, and instruct the lighting device 203 to output the corresponding light and/or instruct the music player 205 to play the corresponding melody.

In the present embodiment, the controller 201 of the atmosphere adjusting device 200 may perform the atmosphere adjusting method described with reference to FIG. 1, so that the atmosphere adjusting device 200 can output the corresponding light and/or melody according to the smell in the room, and thus the light and/or the melody can change with the change of the smell.

In the present embodiment, the lighting device 203, for example, is an LED lamp. In the present embodiment, the music player 205 may obtain music to be played from a local memory or a local library and output it through the speaker, or obtain the music to be played from a network library through the network and output it. In the present embodiment, the smell sensor 207 captures the smell molecules in the air, detects the smell molecules to recognize the smell, and outputs the recognition result of the smell through a signal.

Further, in the present embodiment, the lighting device 203, the music player 205 and the smell sensor 207 are integrated in a device; or at least one of the lighting device 203, the music player 205 or the smell sensor 207 is set as a separate device.

Further, in the present embodiment, the number of each of lighting devices 203 and/or music players 205, and smell sensors 207 is one or multiple. When the number of lighting devices 203 and/or music players 205 and smell sensors 207 is multiple, each of the smell sensors 207 is at a different position and corresponds to at least one lighting device 203 and/or music player 205.

In this way, there may be one-to-one or one-to-multiple correspondence between the smell sensor, and the lighting device and/or the music player, so that an appropriate number of lighting devices and/or music players and smell sensors may be set as needed to better create a harmonious and unified atmosphere in seeing, hearing and smelling for users. Moreover, when multiple smell sensors are at different positions (for example, in different rooms in a home), the controller can also be used to simultaneously control the lights and/or melodies at the different positions to change with the smell, thus enabling the atmosphere adjusting device to adjust the atmospheres of multiple different environments.

For example, when the atmosphere of a family (including the bedroom, the living room and the bathroom) is controlled and adjusted, multiple smell sensors may be arranged at different positions, for example, at the head of the bed in the bedroom, beside the sofa in the living room, beside the toilet in the bathroom, etc. Multiple lighting devices corresponding to the smell sensors may be at the top center of the bedroom, the top center of the living room, and above the door outside the bathroom. Multiple music players corresponding to the smell sensors may be at the head of the bed in the bedroom, the bottom corner of the living room, and above the door outside the bathroom.

In this way, the lighting device 203, the music player 205 and the smell sensor 207 are arranged at the appropriate positions in the home to realize the appropriate adjustment of light/melody with the smell in different rooms in the home.

Furthermore, in the present embodiment, the number of lighting devices 203 and/or music players 205 and smell sensors 207 is one or multiple. When the number of each of lighting devices 203 and/or music players 205 and smell sensors 207 is multiple, each of the lighting devices 203 and/or music players 205 is at the different position and corresponds to at least one smell sensor 207.

In this way, there may be one-to-one or one-to-multiple correspondence between the lighting device and/or the music player, and the smell sensor, so that an appropriate number of lighting devices and/or music players and smell sensors may be set as needed to better create a harmonious and unified atmosphere in seeing, hearing and smelling for users.

Furthermore, in the present embodiment, the atmosphere adjusting device 200 further includes: a position sensor, configured to sense the position of the smell sensor 207 and output the position information of the smell sensor 207. The controller 201 is further configured to obtain the position information of the smell sensor 207, and determine the light and/or the melody to be output from the first corresponding table, according to the position information of the smell sensor 207 and the recognition result of the smell.

In this case, the first corresponding table may include a corresponding relationship between the whole of the position information and the recognition result of the smell, and the light and/or the melody.

In this way, the light and/or the melody to be output is determined by the position information of the smell in combination with the recognition result of the smell, so that different lights and/or melodies can be set for different positions, that is, not only the light and/or the melody in the same room changes with the change of the smell, but also the light and/or the melody in different rooms varies depending on positions.

Furthermore, in the present embodiment, the atmosphere adjusting device 200 further includes: a clock module, configured to output the time information indicating the current time. The time information includes one or more of the following: a season of the year, a day of the week and a time of the day. The controller 201 is further configured to obtain the time information, and determine the light and/or the melody to be output from the first corresponding table, according to the time information and the recognition result of the smell.

In this case, the first corresponding table may indicate a corresponding relationship between the whole of the time information and the recognition result of the smell and the light and/or the melody. The clock module may be located locally or on the network.

In this way, not only the influence of smell on the atmosphere, but also the influence of time on the atmosphere is taken into account, thus enable creating a more harmonious atmosphere after the corresponding light and/or melody is output.

Moreover, the atmosphere adjusting device 200 provided with the smell sensor, the position sensor, the clock module, the lighting device, the music player and the smell diffusing device may be used to output the corresponding light, and/or melody, and/or smell considering the influence of smell, location and time on the atmosphere, thus creating a more harmonious and unified atmosphere in seeing, hearing and smelling for users.

Furthermore, in the present embodiment, the atmosphere adjusting device 200 further includes: one or more other smell sensors within a predetermined distance from the smell sensor 207, each configured to detect an other smell at its position and output the recognition result of the other smell. The controller 201 determines the light and/or the melody to be output from the first corresponding table according to the recognition result of the smell includes: determining the light and/or the melody to be output from the first corresponding table according to the recognition result of the smell and the recognition results of one or more other smells.

In this way, the recognition result of multiple smells within in a predetermined range may be used to accurately obtain the recognition result of the smell within the predetermined range (the smell and one or more other smells are within the predetermined range). For example, multiple smell sensors may be set at different positions in the living room, and the recognition result of the smells in the living room may be accurately determined by multiple recognition results of the smells received from the multiple smell sensors instead of the single recognition result of a smell received from a single smell sensor. Thus, the light and/or the melody corresponding to the smells within the predetermined range may be determined more accurately, so as to create a more harmonious and unified atmosphere.

It is to be noted that the atmosphere adjusting device shown in FIG. 2 may be a light and/or melody adjusting device that adjusts the output light and/or melody based on the detected smell, or a smell adjusting device (or a fragrance adjusting device) that adjusts the output smell based on the detected smell, or a combination of both. An example of the atmosphere adjusting device is an aroma diffuser when it adjusts the light, the melody and the smell based on the detected smell.

Figure 3:
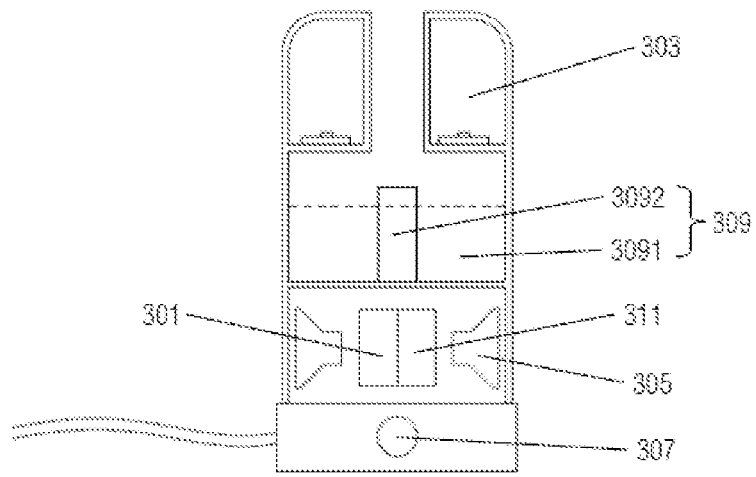
FIG. 3 is a schematic structure diagram of an aroma diffuser according to an embodiment of the present application.

FIG. 3 is a schematic structure diagram of an aroma diffuser according to an embodiment of the present application. As shown in FIG. 3, the aroma diffuser 300 includes: a controller 301, a smell sensor 307, a lighting device 303, a music player 305, an essential oil diffusing device 309, and a memory 311. The controller 301 is configured to perform the atmosphere adjusting method shown in FIG. 1. The smell sensor 307 is configured to detect the smell at its position and output the recognition result of the smell. The lighting device 303 is configured to output light according to the control of the controller 301. The music player is configured to play a melody according to the control of the controller 301. The essential oil diffusing device 309 includes an essential oil storage box 3091 and an essential oil diffuser 3092. The essential oil diffuser 3092 is configured to diffuse the essential oil in the essential oil storage box 3091 according to the control of the controller 301. The memory 311 is configured to store the first corresponding table in advance. The first corresponding table indicates the corresponding relationship between the recognition result of the smell, and the light and/or the melody.

In this way, the aroma diffuser 300 can not only create a desired atmosphere for users by diffusing fragrance to the environment, but also output the corresponding light and/or melody according to the smell (usually the smell of the essential oil when the essential oil of the aroma diffuser is being diffused) of the environment, so that the light and/or the melody can change with the change of the smell, and the atmosphere created by the smell is magnified, thus creating a harmonious and unified atmosphere in seeing, hearing and smelling for users.

Further, in the present embodiment, the essential oil diffusing device 309 adopts any one of thermal diffusion type, spray diffusion type or ultrasonic diffusion type.

In this way, the aroma diffuser 300 adopting any diffusion type of essential oil can perform the above adjustment of light, melody and diffusion smell.

Further, in the present embodiment, the smell of the essential oil includes top note, middle note and base note.

Further, in the present embodiment, the controller 301 determines the light, and/or the melody, and/or the essential oil to be output according to the top note, the middle note and the base note of the essential oil respectively.

In this way, there is a fine change of top note, middle note and base note in the smell of the essential oil diffused into the surrounding environment by the aroma diffuser 300. Thus, by detecting the fine change of the smell of the essential oil through the smell sensor 307, the light, and/or the melody, and/or the essential oil output by the aroma diffuser 300 can reflect the fine change in the smell of the essential oil, thereby not only creating a harmonious and unified atmosphere in seeing, hearing and smelling for users, but also bringing users a more immersive experience.

Moreover, in the present embodiment, the smell sensor 307 is on the external surface of the aroma diffuser to detect the smell in the external environment of the aroma diffuser. However, the smell sensor 307 may also be located inside the aroma diffuser.

Figure 4:
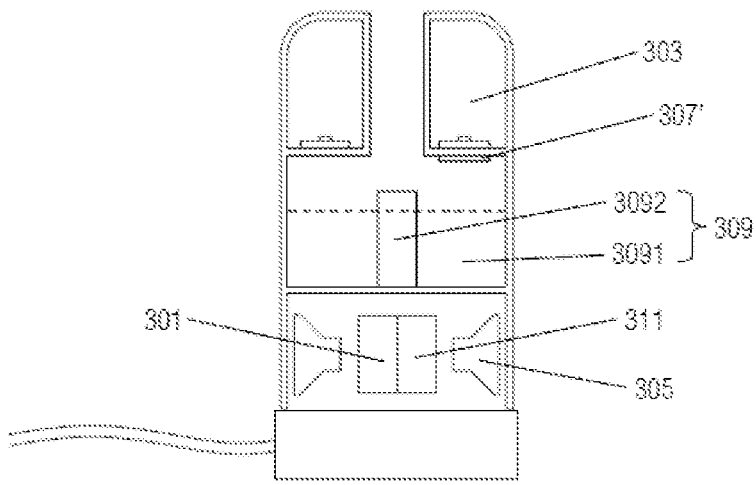
FIG. 4 is another schematic structure diagram of an aroma diffuser according to an embodiment of the present application.

FIG. 4 is another schematic structure diagram of an aroma diffuser according to an embodiment of the present application. The structure of the aroma diffuser shown in FIG. 4 is basically the same as that shown in FIG. 3, and the only difference therebetween is that the smell sensor 307' of the aroma diffuser 400 shown in FIG. 4 is located on the top surface inside the essential oil storage box 3091 in the aroma diffuser 400. This position is on the diffusion path of the essential oil within the essential oil storage box 3091, so that the smell sensor 307' can detect the smell of the essential oil stored in the internal environment of the aroma diffuser 400 (that is, the smell in the internal environment of the aroma diffuser 400).

It is to be noted that the smell sensor 307' is not necessarily restricted to this position, but may be located at any position along the diffusion path of the essential oil in the aroma diffuser 400, as long as the smell sensor 307' may detect the smell in the internal environment of the aroma diffuser 400 at that position.

In this way, the aroma diffuser 400 shown in FIG. 4 can determine the light, and/or the melody, and/or the essential oil to be output according to the smell in the internal environment of the aroma diffuser 400, so as to make the output light, the played melody and the diffused essential oil harmonious and unified.

Moreover, by detecting the smell of the essential oil stored in the internal environment of the aroma diffuser 400 through the smell sensor 307', the controller 301 of the aroma diffuser 400 may obtain the diffusion concentration of the essential oil in the aroma diffuser 400, thus obtaining the diffusion rate of the essential oil in the aroma diffuser 400, to adjust the diffusion rate of the essential oil.

Moreover, it may also be conceived to set an additional smell sensor on the external surface of the aroma diffuser 400 to detect the smell in the external environment of the aroma diffuser. In this case, the aroma diffuser 400 may choose to output the corresponding light, and/or melody, and/or essential oil according to the smell in its external environment; or output the corresponding light, and/or melody, and/or essential oil according to the smell in its internal environment; or determine some properties of the light, and/or the melody, and/or the essential oil to be output according to the smell in its external environment, and determine some other properties of the light, and/or the melody, and/or the essential oil to be output according to the smell in its internal environment, so as to create a desired atmosphere through the implementation of various outputs of the light, and/or the melody, and/or the essential oil.

In the above embodiments of the present application, the descriptions of the embodiments focus on different aspects. A part which is not described in a certain embodiment in detail may refer to the related description of the other embodiments.

In the several embodiments provided in the application, it is to be understood that the technical contents disclosed may be realized in other ways. The embodiment of the device described above is only schematic; for example, the division of the units or modules is only a division of logical functions, and there may be other dividing modes during the actual implementation, for example, multiple units or modules or components may be combined or integrated to another system, or some features may be ignored or are not executed.

The above is only the preferred embodiments of the present application; it should be indicated that, on the premise of not departing from the principles of the present application, those of ordinary skill in the art may also make a number of improvements and supplements, and these improvements and supplements should fall within the protection scope of the present application.

What is claimed is:

1. An atmosphere adjusting method, comprising:
   receiving a recognition result of a smell for a specific position;
   obtaining a first corresponding table that indicates a corresponding relationship between the recognition result of the smell and light and/or melody;
   determining the light and/or the melody to be output from the first corresponding table, according to the recognition result of the smell; and
   instructing output of the corresponding light and/or melody in the specific position wherein an output of the light and/or the melody dynamically changes with a change in the smell.

2. The atmosphere adjusting method according to claim 1, wherein the recognition result of the smell comprises one or more of the following: smell molecules contained in the smell, a category to which the smell belongs, and a concentration of the smell.

3. The atmosphere adjusting method according to claim 2, wherein determining the light and/or the melody to be output from the first corresponding table according to the recognition result of the smell comprises:
   determining, from the first corresponding table, properties of the light and/or the melody corresponding to the smell molecules contained in the smell, and/or the category to which the smell belongs, and/or the concentration of the smell; and
   determining the light and/or the melody to be output according to the determined properties of the light and/or the melody;
   wherein, the properties of the light comprise one or more of the following: color, lighting direction, degree of flicker and intensity, and the properties of the melody comprise one or more of the following: theme, genre, rhythm, pitch and intensity.

4. The atmosphere adjusting method according to claim 3, wherein the first corresponding table comprises a corresponding relationship between a combination of more than two kinds of smell molecules and the properties of the light and/or the melody.

5. The atmosphere adjusting method according to claim 4, wherein the recognition result of the smell comprises a plurality of kinds of smell molecules contained in the smell, and determining the properties of the light and/or the melody corresponding to the smell molecules contained in the smell, and/or the category to which the smell belongs, and/or the concentration of the smell from the first corresponding table comprises:
   determining the properties of the light and/or the melody corresponding to the combinations of the plurality of kinds of smell molecules, from the first corresponding table.

6. The atmosphere adjusting method according to claim 3, wherein the recognition result of the smell comprises a plurality of kinds of smell molecules contained in the smell and the concentration of the smell, the concentration of the smell comprising the concentration of each kind of smell molecules in the plurality of kinds of smell molecules, and determining the properties of the light and/or the melody corresponding to the smell molecules contained in the smell, and/or the category to which the smell belongs, and/or the concentration of the smell from the first corresponding table comprises:
   determining the category to which the smell belongs from the first corresponding table according to the plurality of kinds of smell molecules and the concentration of each kind of smell molecules; and
   further determining the properties of the light and/or the melody corresponding to the category to which the smell belongs from the first corresponding table.

7. The atmosphere adjusting method according to claim 3, wherein determining the properties of the light and/or the melody corresponding to the smell molecules contained in the smell, and/or the category to which the smell belongs, and/or the concentration of the smell from the first corresponding table further comprises:
   according to a preset user preference, determining the properties of the light and/or the melody corresponding to the smell molecules contained in the smell, and/or the category to which the smell belongs, and/or the concentration of the smell from the first corresponding table.

8. The atmosphere adjusting method according to claim 2, wherein determining the light and/or the melody to be output from the first corresponding table according to the recognition result of the smell comprises:
  determining whether the concentration of the smell is higher than a preset first threshold or lower than a preset second threshold, the first threshold being greater than the second threshold; and
  when the concentration of the smell is higher than the first threshold, determining that the light and/or the melody to be output is a predetermined warning light and/or a warning tone; or
  when the concentration of the smell is lower than the second threshold, determining that the light and/or the melody to be output is a predetermined prompt light and/or a prompt tone.

9. The atmosphere adjusting method according to claim 2, further comprising:
  obtaining a second corresponding table that indicates a corresponding relationship between the recognition result of the smell and a smell to be diffused;
  determining a diffusion smell to be diffused from the second corresponding table, according to the recognition result of the smell; and
  instructing diffusion of the diffusion smell.

10. The atmosphere adjusting method according to claim 9, wherein instructing diffusion of the diffusion smell further comprises:
  when the concentration of the smell received is lower than a preset third threshold, controlling the increase of a diffusion rate of the diffusion smell until the concentration of the smell received reaching the third threshold; and
  when the concentration of the smell received is higher than a preset fourth threshold, controlling the decrease of the diffusion rate of the diffusion smell until the concentration of the smell received is equal to or lower than the fourth threshold, the fourth threshold being greater than the third threshold.

11. The atmosphere adjusting method according to claim 1, further comprising:
  obtaining position information of the specific position; and
  wherein determining the light and/or the melody to be output from the first corresponding table according to the recognition result of the smell comprises:
    determining the light and/or the melody to be output from the first corresponding table, according to the position information and the recognition result of the smell.

12. The atmosphere adjusting method according to claim 1, further comprising:
  receiving a recognition result of one or more other smells for one or more other positions within a predetermined distance from the specified position; and
  determining the light and/or the melody to be output from the first corresponding table according to the recognition result of the smell comprises:
    determining the light and/or the melody to be output from the first corresponding table, according to the recognition result of the smell for the specific position and the recognition result of one or more other smells for one or more other positions.

13. The atmosphere adjusting method according to claim 1, further comprising:
  obtaining time information indicating the current time; the time information comprising one or more of the following: a season of the year, a day of the week and a time of the day; and
  wherein determining the light and/or the melody to be output from the first corresponding table according to the recognition result of the smell comprises: determining the light and/or the melody to be output from the first corresponding table according to the time information and the recognition result of the smell.

14. An aroma diffuser, comprising:
  a controller, configured to perform the method according to claim 1;
  a smell sensor, configured to detect a smell at its position and output a recognition result of the smell;
  a lighting device, configured to output light according to the control of the controller;
  a music player, configured to play a melody according to the control of the controller;
  an essential oil diffusing device, comprising an essential oil storage box and an essential oil diffuser which is configured to diffuse the essential oil in the essential oil storage box according to the control of the controller; and
  a memory, stored with a first corresponding table in advance, the first corresponding table indicating a corresponding relationship between the recognition result of the smell and the light and/or the melody.

15. The aroma diffuser according to claim 14, wherein the smell of the essential oil comprises top note, middle note and base note.

16. The aroma diffuser according to claim 15, wherein the controller determines the light, and/or the melody, and/or the essential oil to be output according to the top note, the middle note and the base note of the essential oil respectively.

17. The aroma diffuser according to claim 14, wherein,
  the position of the smell sensor is any position on the outer surface of the aroma diffuser, so as to detect the smell outside of the aroma diffuser; or
  the position of the smell sensor is any position on a diffusion path of the essential oil in the aroma diffuser, so as to detect the smell inside the aroma diffuser.

18. An atmosphere adjusting device, comprising:
  a controller;
  a smell sensor, configured to detect a smell at its position and output a recognition result of the smell;
  a lighting device and/or a music player, the lighting device is configured to output light according to the control of the controller, and the music player is configured to play a melody according to the control of the controller; and
  a memory, stored with a first corresponding table in advance, the first corresponding table indicating a corresponding relationship between the recognition result of the smell and the light and/or the melody;
  wherein the controller is configured to:
    receive the recognition result of the smell;
    obtain the first corresponding table from the memory;
    according to the recognition result of the smell, determine the light and/or the melody to be output from the first corresponding table; and
    instruct the lighting device to output the light, and/or instruct the music player to play the melody wherein an output of the light and/or the melody dynamically changes with a change in the smell.

19. The atmosphere adjusting device according to claim 18, wherein the lighting device, the music player and the smell sensor are integrated in one device; or at least one of the lighting device, the music player or the smell sensor is set as a separate device.

20. The atmosphere adjusting device according to claim 18, wherein the number of each of lighting devices and/or music players, and smell sensors is one or multiple, and
when the number of each of lighting devices and/or music players and smell sensors is multiple, each of the smell sensors is at a different position and corresponds to at least one lighting device and/or music player.

21. The atmosphere adjusting device according to claim 18, wherein the number of each of lighting devices and/or music players and smell sensors is one or multiple, and
when the number of each of lighting devices and/or music players and smell sensors is multiple, each of the lighting devices and/or the music players is at a different position and corresponds to at least one smell sensor.

22. The atmosphere adjusting device according to claim 18, wherein the recognition result of the smell comprises one or more of the following: smell molecules contained in the smell, a category to which the smell belongs, and a concentration of the smell.

23. The atmosphere adjusting device according to claim 22, wherein determining, by the controller, the light and/or the melody to be output from the first corresponding table according to the recognition result of the smell comprises:
determining, by the controller, properties of the light and/or the melody corresponding to the smell molecules contained in the smell, and/or the category to which the smell belongs, and/or the concentration of the smell from the first corresponding table; and
determining the light and/or the melody to be output according to the determined properties of the light and/or the melody;
wherein, the properties of the light comprise one or more of the following: color, lighting direction, degree of flicker and intensity, and the properties of the melody comprise one or more of the following: theme, genre, rhythm, pitch and intensity.

24. The atmosphere adjusting device according to claim 23, wherein the first corresponding table comprises a corresponding relationship between a combination of more than two kinds of smell molecules and the properties of the light and/or the melody.

25. The atmosphere adjusting device according to claim 24, wherein the recognition result of the smell comprises a plurality of kinds of smell molecules contained in the smell, and determining, by the controller, the properties of the light and/or the melody corresponding to the smell molecules contained in the smell, and/or the category to which the smell belongs, and/or the concentration of the smell from the first corresponding table comprises:
determining, by the controller, the properties of the light and/or the melody corresponding to the combinations of the plurality of kinds of smell molecules from the first corresponding table.

26. The atmosphere adjusting device according to claim 23, wherein the recognition result of the smell comprises a plurality of kinds of smell molecules contained in the smell and the concentration of the smell, the concentration of the smell comprising the concentration of each kind of smell molecules in the plurality of kinds of smell molecules, and determining, by the controller, the properties of the light and/or the melody corresponding to the smell molecules contained in the smell, and/or the category to which the smell belongs, and/or the concentration of the smell from the first corresponding table comprises:
determining the category to which the smell belongs from the first corresponding table, according to the plurality of kinds of smell molecules and the concentration of each kind of smell molecules; and
further determining the properties of the light and/or the melody corresponding to the category to which the smell belongs, from the first corresponding table.

27. The atmosphere adjusting device according to claim 23, wherein determining, by the controller, the properties of the light and/or the melody corresponding to the smell molecules contained in the smell, and/or the category to which the smell belongs, and/or the concentration of the smell from the first corresponding table further comprises:
according to a preset user preference, determining the properties of the light and/or the melody corresponding to the smell molecules contained in the smell, and/or the category to which the smell belongs, and/or the concentration of the smell from the first corresponding table.

28. The atmosphere adjusting device according to claim 22, wherein determining, by the controller, the light and/or the melody to be output from the first corresponding table according to the recognition result of the smell comprises:
determining, by the controller, whether the concentration of the smell is higher than a preset first threshold or lower than a preset second threshold, the first threshold being greater than the second threshold; and
when the concentration of the smell is higher than the first threshold, determining that the light and/or the melody to be output is a predetermined warning light and/or a warning tone; or
when the concentration of the smell is lower than the second threshold, determining that the light and/or the melody to be output is a predetermined prompt light and/or a prompt tone.

29. The atmosphere adjusting device according to claim 22, further comprising:
a smell diffusing device, configured to diffuse the smell according to the control of the controller; and the memory also stored with a second corresponding table that indicates a corresponding relationship between the recognition result of the smell and the smell to be diffused in advance;
wherein, the controller is further configured to:
obtain the second corresponding table;
determine a diffusion smell to be diffused from the second corresponding table according to the recognition result of the smell; and
instruct the smell diffusing device to diffuse the diffusion smell.

30. The atmosphere adjusting device according to claim 29, wherein instructing the smell diffusing device to diffuse the diffusion smell further comprises:
when the concentration of the smell received is lower than a preset third threshold, controlling the smell diffusing device to increase a diffusion rate of the diffusion smell until the concentration of the smell received reaching the third threshold; and
when the concentration of the smell received is higher than a preset fourth threshold, controlling the smell diffusing device to decrease the diffusion rate of the diffusion smell until the concentration of the smell received being equal to or lower than the fourth threshold, the fourth threshold being greater than the third threshold.

31. The atmosphere adjusting device according to claim 18, further comprising:
   a position sensor, configured to sense the position of the smell sensor and output position information of the smell sensor;
   wherein, the controller is further configured to:
   obtain the position information of the smell sensor, and
   determine the light and/or the melody to be output from the first corresponding table, according to the position information of the smell sensor and the recognition result of the smell.

32. The atmosphere adjusting device according to claim 18, further comprising:
   a clock module, configured to output time information indicating the current time; the time information comprises one or more of the following: a season of the year, a day of the week and a time of the day; and
   wherein the controller is further configured to:
   obtain the time information; and
   determine the light and/or the melody to be output from the first corresponding table, according to the time information and the recognition result of the smell.

33. The atmosphere adjusting device according to claim 18, further comprising:
   one or more other smell sensors within a predetermined distance from the smell sensor, each configured to detect another smell at its position and output the recognition result of the other smell; and
   determining, by the controller, the light and/or the melody to be output from the first corresponding table according to the recognition result of the smell comprises:
   determining the light and/or the melody to be output from the first corresponding table according to the recognition result of the smell and the recognition results of one or more other smells.

34. The atmosphere adjusting device according to claim 18, wherein the memory is a local memory or a network memory.

* * * * *